(12) United States Patent
Kimura et al.

(10) Patent No.: US 10,492,887 B2
(45) Date of Patent: *Dec. 3, 2019

(54) MEDICINE INGESTION STATE MANAGEMENT METHOD, MEDICINE AND MEDICINE INGESTION STATE MANAGEMENT DEVICE

(71) Applicant: FUJITSU LIMITED, Kawasaki-shi, Kanagawa (JP)

(72) Inventors: Hitoshi Kimura, Kawasaki (JP); Morihito Notani, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 796 days.

This patent is subject to a terminal disclaimer.

(21) Appl. No.: 15/006,274

(22) Filed: Jan. 26, 2016

(65) Prior Publication Data

US 2016/0135918 A1 May 19, 2016

Related U.S. Application Data

(63) Continuation of application No. 11/360,396, filed on Feb. 24, 2006, now Pat. No. 9,913,698, and a
(Continued)

(51) Int. Cl.
*A61B 90/98* (2016.01)
*G06Q 10/10* (2012.01)
(Continued)

(52) U.S. Cl.
CPC ............. *A61B 90/98* (2016.02); *A61B 5/073* (2013.01); *A61B 5/411* (2013.01); *A61B 5/4833* (2013.01);
(Continued)

(58) Field of Classification Search
CPC ........ G16H 10/00; G16H 10/40; G16H 15/00; G16H 20/00; G16H 20/10; G16H 20/13;
(Continued)

(56) References Cited

U.S. PATENT DOCUMENTS 5,925,030 A * 7/1999 Gross .................. A61K 9/0009
604/141
6,294,999 B1 9/2001 Yarin et al.
(Continued)

FOREIGN PATENT DOCUMENTS

JP 07-111985 5/1995
JP 2002-102310 4/2002
(Continued)

OTHER PUBLICATIONS

CTFR—Final Office Action dated Apr. 14, 2017 issued in the corresponding U.S. Appl. No. 11/360,396.
(Continued)

*Primary Examiner* — Robert W Morgan
*Assistant Examiner* — Charles P Coleman
(74) *Attorney, Agent, or Firm* — Fujitsu Patent Center

(57) ABSTRACT

Disclosed is a medicine ingestion state management method capable of objectively managing medicine ingestion states of patients. The medicine ingestion state management method involves an operation of prescribing medicine (10) encapsulating, together with a medicament, a medicine information transmitting unit (20) having a function of transmitting medicine information capable of specifying a type and a quantity of the medicament to each individual patient, and an operation of grasping the medicine ingestion state of each patient by collecting the medicine information from each medicine information transmitting unit (20) in each patient.

12 Claims, 11 Drawing Sheets

Related U.S. Application Data continuation of application No. PCT/JP03/11199, filed on Sep. 2, 2003.

(51) Int. Cl.
| | |
|---|---|
| *G16H 20/13* | (2018.01) |
| *A61B 5/07* | (2006.01) |
| *A61B 5/00* | (2006.01) |
| *G06F 19/00* | (2018.01) |
| *G16H 10/60* | (2018.01) |
| *A61J 3/00* | (2006.01) |

(52) U.S. Cl.
CPC ........ *A61B 5/4839* (2013.01); *G06F 19/3462* (2013.01); *G06Q 10/10* (2013.01); *G16H 10/60* (2018.01); *G16H 20/13* (2018.01); *A61J 3/007* (2013.01)

(58) Field of Classification Search
CPC ........ G16H 20/17; G16H 30/00; G16H 40/00; G16H 50/00; G16H 70/00; G16H 80/00; G16H 10/60; A61B 90/98; A61B 5/073; A61B 5/411; A61B 5/4833; A61B 5/4839; G06F 19/3462; G06Q 10/10; A61J 3/007
USPC .................................................. 705/2, 3, 20
See application file for complete search history.

(56) References Cited

U.S. PATENT DOCUMENTS

| | | | | |
|---|---|---|---|---|
| 6,380,858 | B1 | 4/2002 | Yarin et al. | |
| 7,160,258 | B2* | 1/2007 | Imran ................ | A61B 1/00082 600/424 |
| 2002/0099310 | A1 | 7/2002 | Kimchy et al. | |
| 2002/0132226 | A1 | 9/2002 | Nair et al. | |
| 2003/0109830 | A1* | 6/2003 | Picha ................ | A61J 15/0015 604/174 |
| 2003/0229517 | A1 | 12/2003 | Meserol et al. | |
| 2005/0147559 | A1 | 7/2005 | Von Alten | |

FOREIGN PATENT DOCUMENTS

| | | |
|---|---|---|
| JP | 2002-109070 | 4/2002 |
| JP | 2002-230182 | 8/2002 |
| JP | 2003-144417 | 5/2003 |
| JP | 2003-518410 | 6/2003 |
| WO | 01/47466 | 7/2001 |

OTHER PUBLICATIONS

NOA—Notice of Allowance dated Oct. 23, 2017 issued in the parent U.S. Appl. No. 11/360,396 [allowed].

Japanese Office Action dated Mar. 17, 2009 in corresponding Japanese Patent Application 2005-508772.

USPTO, (Coleman) Non-Final Rejection, dated Nov. 10, 2014, in parent U.S. Appl. No. 11/360,396 [pending].

USPTO, (Coleman) Non-Final Rejection, dated May 27, 2014, in parent U.S. Appl. No. 11/360,396 [pending].

USPTO, (Coleman) Non-Final Rejection, dated Jun. 20, 2013, in parent U.S. Appl. No. 11/360,396 [pending].

USPTO, (Coleman) Non-Final Rejection, dated Jul. 21, 2009, in parent U.S. Appl. No. 11/360,396 [pending].

USPTO, (Coleman) Final Rejection, dated Aug. 5, 2015, in parent U.S. Appl. No. 11/360,396 [pending].

USPTO, (Coleman) Final Rejection, dated Oct. 9, 2013, in parent Appl. No. 11/360,396 [pending].

USPTO, (Coleman) Final Rejection, dated Mar. 26, 2010, in parent U.S. Appl. No. 11/360,396 [pending].

International Search Report, mailed in connection with PCT/JP2003/11199 and dated Dec. 9, 2003.

USPTO, (Coleman) Non-Final Rejection, dated Aug. 16, 2016, in parent U.S. Appl. No. 11/360,396 (pending).

CTAV—Advisory Action dated Sep. 6, 2017 issued in the corresponding U.S. Appl. No. 11/360,396.

CTNF—Non-Final Rejection dated May 31, 2018 in related U.S. Appl. No. 15/006,291 [pending].

NOAR—Notice of Allowance dated Jan. 28, 2019 in related U.S. Appl. No. 15/006,291 [allowed].

* cited by examiner

FIG. 5

| | |
|---|---|
| MEDICINE ID-CODE | ; @117 |
| PRODUCT NAME | ; MICARUDIS 20 mg |
| PHARMACEUTICAL COMPANY | ; MEDICINE A |
| CLASSIFICATION | ; ANTIHYPERTENSIVE DRUG, |
| INGREDIENT/POTENCY | ; TERMISARUSAN 20 mg, ... |
| DOSAGE | ; FOR ADULT, 40 mg, ONE DOSE PER DAY, ... |
| IN-VIVO EFFECTIVE PERIOD | ; APPROXIMATELY 24 HOURS, |
| ADVERSE DRUG ACTION | ; NOTHING PARTICULAR, |
| UNCOMBINABLE MEDICINE/INGREDIENT | ; @198. @354, INGREDIENT A, INGREDIENT C, ... |
| ⋮ | ⋮ |

FIG. 6

| | |
|---|---|
| PATIENT ID | ; 00001035AF27 |
| BASIC INFORMATION | ; NAME, FUJITSU HANAKO, DISTINCTION OF SEX; FEMALE, |
| MEDICAL RECORD | ; 2001.02.05 OO-SYMPTOM |
| ALLERGY | ; NOTHING |
| PREGNANCY | ; NOT PREGNANT |
| PRESCRIPTION RECORD INFO. | ; PRESCRIPTION INFO. 1, PRESCRIPTION INFO. 2, |
| INGESTIONS STATE EXAMINATION RECORD INFO. | ; EXAM-RESULT INFO. 1, EXAM-RESULT INFO. 2, |
| ⋮ | ⋮ |

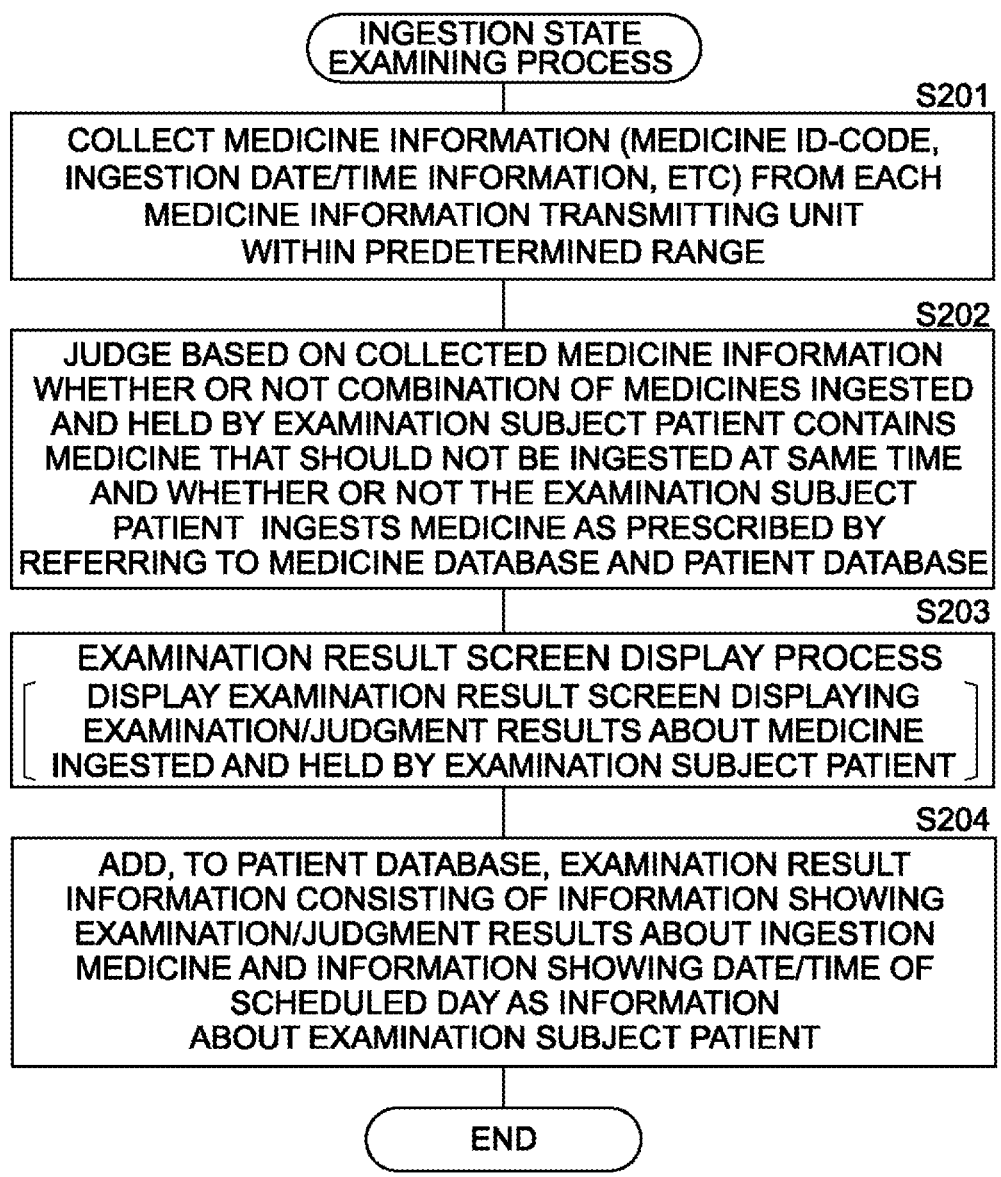

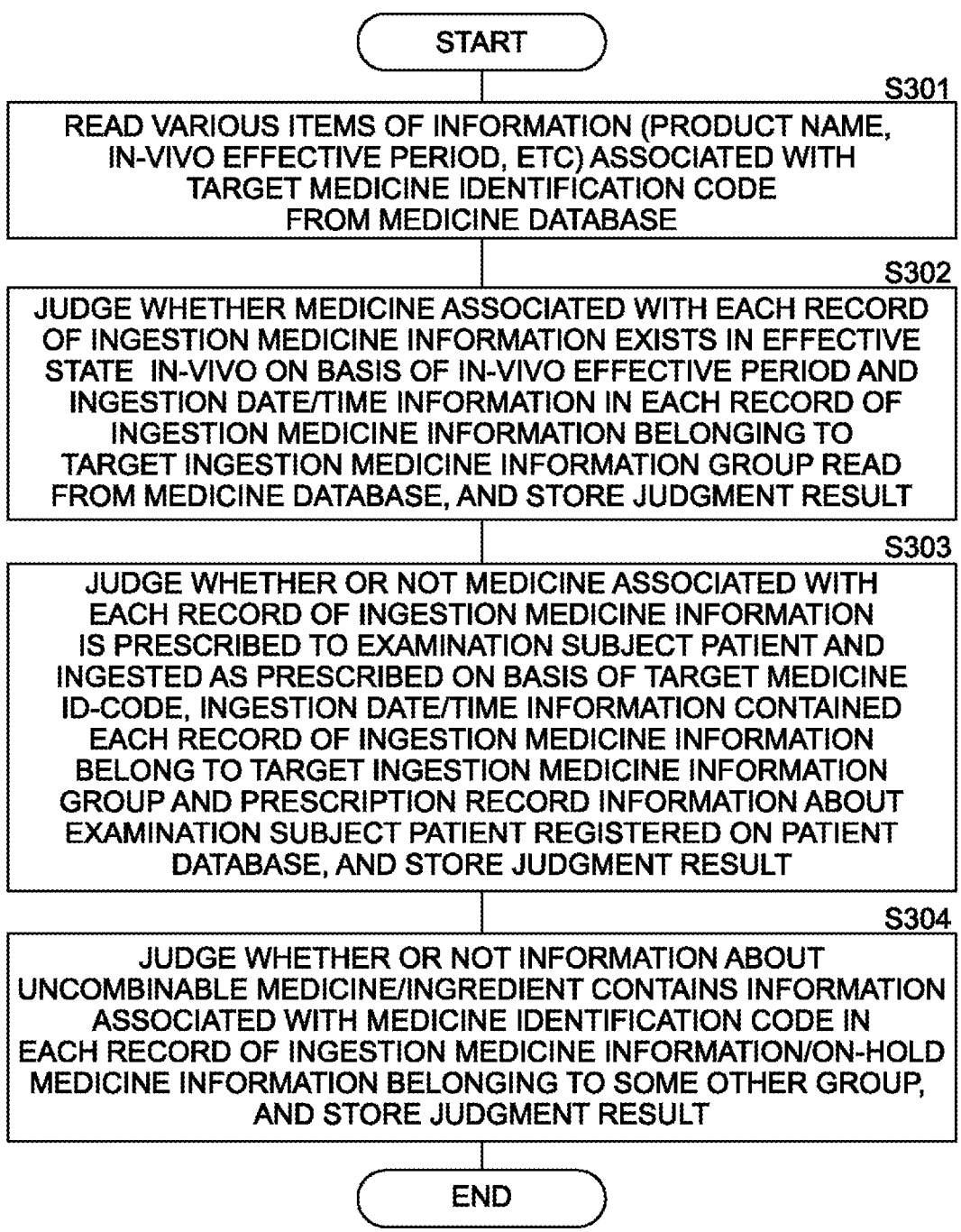

FIG. 9

INGESTION MEDICINE/ON-HOLD MEDICINE
EXAMINATION RESULT (MR./MRS./MISS. XX)

INGESTION MEDICINE STATE

| NAME | POTENCY (PER CAPSULE) | IN-VIVO EFFECTIVE MEDICINE QUANTITY | INGESTION STATE | REMARKS |
|---|---|---|---|---|
| xxxxx | INGREDIENT A 30 mg,... | FOR ONE CAPSULE | 2003/7/1,20:05 2003/7/3,19:55 | AS PRESCRIBED (SENSITIVE MEDICINE; ZZZZ) |
| yyyyy | INGREDIENT B 10 mg,... | FOR TWO CAPSULES | 2003/7/1,20:03 2003/7/3,09:55 2003/7/3,19:54 | INGESTION FREQUENCY ABNORMAL |

ON-HOLD MEDICINE STATE

| NAME | POTENCY (PER CAPSULE) | NUM. | REMARKS |
|---|---|---|---|
| xxxxx | INGREDIENT B 30 mg, ... | 3 | |
| zzzzz | INGREDIENT D 10 mg, ... | 5 | OUT-OF-PRESCRIPTION MEDICINE, UNUSABLE SIMULTANEOUSLY WITH XXXX |

[REEXAMINATION]  [PRESCRIPTION INPUT SCREEN]

MEDICINE INGESTION STATE MANAGEMENT METHOD, MEDICINE AND MEDICINE INGESTION STATE MANAGEMENT DEVICE

CROSS-REFERENCE TO RELATED APPLICATION

This application is a continuation of application Ser. No. 11/360,396, filed Feb. 24, 2006, which is a continuation application, filed under 35 U.S.C. § 111(a), of International Application PCT/JP2003/011199, filed Sep. 2, 2003, the contents of which are incorporated herein by reference.

TECHNICAL FIELD

The present invention relates to a medicine ingestion state management method, a medicine ingestion state management device and a medicine that are used for objectively managing a medicine ingestion state of a patient.

BACKGROUND ARTS

As known well, over the recent years, the great majority of hospitals have been using databases for managing which medicine was prescribed to each individual patient. Further, there was proposed a technology of attaching, to the patient, a wrist band fitted with an IC tag (transponder) recorded with identifying information etc of the patient in order to prevent the patient (inpatient) and a medical material to be mistreated (in order not to misuse information on the database) (refer to, e.g., Patent document 1, Patent document 2).
Patent document 1 Japanese Patent Application Laid-Open Publication No. 2002-230182
Patent document 2 Japanese Patent Application Laid-Open Publication No. 2002-109070

Now, information necessary for conducting proper prescription is information about a type and a quantity of the medicine that is actually ingested by the patient, however, none of the databases (i.e., the existing databases employed in the medical field) employed for the technology described above is stored with any information on persons who are not outpatients to the self-hospital, and each of these databases is stored with information merely about the medicine of which ingestion is instructed to each of the outpatients to the self-hospital.

Namely, the existing database used in the medical field is stored with none of the information about the patients who are not the outpatients (nor the inpatients) to the self-hospital and is not stored, though stored with the information serving as key information for determining a content of the prescription for each of the outpatients to the self-hospital, with all necessary items of information for conducting the proper prescription.

Therefore, when determining the content of the prescription for a certain patient, even if this patient is the outpatient to the self-hospital, there is a necessity of diagnostically interviewing the outpatient about what type of medicine is ingested (about whether the prescribed medicine is actually ingested or not).

Then, in response to this diagnostic interview, if the outpatient accurately reports the name and the quantity of the ingested medicine, it follows that a proper medicine is to be prescribed to the outpatient. Whereas if the outpatient does not precisely memorize the name and the quantity of the medicine ingested by the outpatient or if the patient gets unconscious, there were a case of prescribing to the patient a medicine incompatible to the medicine that is actually ingested by the patient and a case of giving an excessive dosage of the medicine to the patient.

DISCLOSURE OF THE INVENTION

Such being the case, it is an object of the present invention to provide a medicine ingestion state management method, a medicine ingestion state management device and a medicine each capable of objectively managing a medicine ingestion state of a patient.

A medicine ingestion state management method according to a first mode of the present invention that is devised to solve the problems given above is a method of acquiring a medicine ingestion state of a patient via wireless communications between a medicine encapsulating, together with a medicament, a medicine information transmitting unit having a function of transmitting medicine information defined as information capable of specifying a type and a quantity of the medicament and a computer including a wireless communication device and accessible to a database stored with the medicine information and the type and the quantity of the medicament in a way that associates these items of information with each other, wherein the computer sequentially executes a medicine information collecting step of receiving and collecting, through the wireless communication device, the medicine information transmitted by the each medicine information transmitting unit existing within a space within a predetermined range including the patient; and a gasping step of grasping the ingestion state of the patient by accessing the database and reading the type and the quantity of the medicament associated with each record of medicine information collected in the medicine information collecting step.

Similarly, a medicine ingestion state management device according to the first mode of the present invention is a device for managing a patient's ingestion state of a medicine encapsulating, together with a medicament, a medicine information transmitting unit having a function of transmitting medicine information defined as information capable of specifying a type and a quantity of the medicament, the device comprising medicine information receiving means receiving the medicine information transmitted by each medicine information transmitting unit existing in a space within a predetermined range including the patient, searching means accessing a database stored with the medicine information and a type and a quantity of the medicament in a way that associates these items of information with each other and reading the type and the quantity of the medicament associated with each record of medicine information received by the medicine information receiving means, and information output means outputting the information representing the type and the quantity of the medicament that are read by the searching means.

According to the medicine ingestion state management method and the medicine ingestion state management device, it is possible to grasp what type of medicine is ingested by the patient without hearing the patient himself or herself about the information on the medicine ingested by the patient. Accordingly, the use of the medicine ingestion state management method and the medicine ingestion state management device makes it possible to prevent the patient from being given prescription of a medicine incompatible to the medicine that is actually ingested by the patient, and to prevent an excessive dosage of the medicine to the patient.

It should be noted that when carrying out the medicine ingestion state management method, each medicine information transmitting unit be, it is desirable, configured so as to change a mode of transmitting the medicine information from a mode kept so far when the self-unit enters a predetermined in-vivo part. The reason why so is that this change is a piece of information showing a fact of the ingestion, since the medicine is not yet ingested, an already-ingested medicine can be distinguished from the medicine existing outside the body of the patient. Specifically, the mode may be changed so that the medicine information contains information corresponding to an ingestion date/time. From such a piece of information corresponding to the ingestion date/time, it can be specified as to whether the medicament in the medicine is now within an in-vivo effective period or not, and hence this information is useful for determining what type of medicament is prescribed.

Further, a medicine ingestion state management method according to another mode of the present invention is a method of acquiring a medicine ingestion state of a patient via wireless communications between a medicine encapsulating, together with a medicament, a first type medicine information transmitting unit having a function of transmitting medicine information defined as information capable of specifying a type and a quantity of the medicament, and a second type medicine information transmitting unit having a function of transmitting second identifying information associated with first identifying information transmitted by the first type medicine information transmitting unit and coming to a status of not transmitting the second identifying information after the self-unit has entered a specified in-vivo part, and a computer including a wireless communication device and accessible to a database stored with the medicine information and the type and the quantity of the medicament in a way that associates these items of information with each other, wherein the computer sequentially executes a medicine information collecting step of making the computer collect the medicine information and the first identifying information transmitted by the first type medicine information transmitting unit existing within a space within a predetermined range including the patient' body, and the second identifying information transmitted by the second type medicine information transmitting unit, and a gasping step of grasping the ingestion state of the patient by making the computer access the database and read, in the various items of medicine information collected in the medicine information collecting step, the type and the quantity of the medicament associated with the medicine information containing the second identifying information corresponding to the first identifying information transmitted from the same first type medicine information transmitting unit but not collected in the medicine information collecting step.

Similarly, a medicine ingestion state management device according to a second mode of the present invention is a device for managing a patient's ingestion state of a medicine encapsulating, together with a medicament, a first type medicine information transmitting unit having a function of transmitting medicine information defined as information capable of specifying a type and a quantity of the medicament, and a second type medicine information transmitting unit having a function of transmitting second identifying information associated with first identifying information transmitted by the first type medicine information transmitting unit and coming to a status of not transmitting the second identifying information after the self-unit has entered a specified in-vivo part, the medicine ingestion state management device comprising medicine information receiving means receiving the medicine information and the first identifying information transmitted by the first type medicine information transmitting unit existing within a space within a predetermined range including the patient, and the second identifying information transmitted by the second type medicine information transmitting unit, searching means accessing a database stored with the medicine information and a type and a quantity of the medicament in a way that associates these items of information with each other, and reading, in the medicine information received by the medicine information receiving means, the type and the quantity of the medicament associated with the medicine information containing the second identifying information corresponding to the first identifying information transmitted from the same first type medicine information transmitting unit but not received by the medicine information receiving means, and information output means outputting information representing the type and the quantity of the medicament that are read by the searching means.

According to the medicine ingestion state management method and the medicine ingestion state management device described above, it is possible to grasp what type of medicine is ingested by the patient without hearing the patient himself or herself about the information on the medicine ingested by the patient and grasp whether or not this medicine reaches a predetermined in-vivo part where a medicine effect thereof can exhibit. Accordingly, the use of the medicine ingestion state management method and the medicine ingestion state management device makes it possible to prevent the patient from being given prescription of a medicine incompatible to the medicine that is actually ingested by the patient and exhibits the medicine effect, and to prevent an excessive dosage of the medicine to the patient.

Moreover, when using in combination an in-vivo effective period representing a period during which ingredients of the medicine keep effectiveness thereof after the ingestion and ingestion date/time information acquired from the medicine information transmitting unit, which are stored beforehand on the database in a way that associates these items of information with each record of medicine information, the ingredients of the medicine of which the effect does not yet expire within the body of the patient can be known. Hence, the prescription can be made by collating the ingredients of this medicine with ingredients of a scheduled-to-be-prescribed medicine, and it is therefore feasible to prevent the patient from being given prescription of a medicine incompatible to the medicine that is actually ingested by the patient and actually exhibits the medicine effect, and to prevent an excessive dosage of the medicine to the patient.

It should be noted that the medicine information transmitting unit transmitting the medicine information containing the ingestion date/time information can involve using a unit including, for example, detection means detecting that the unit enters a body, date/time specifying means specifying a date/time when the detection means detects that the unit enters the body, and means transmitting information associated with the type and the quantity of the medicament occluded together with the self-unit and the medicine information containing ingestion date/time information representing a date/time specified by the date/time specifying means. It should be noted that this detection means can involve employing means detecting that the unit enters the body when the medicine information transmitting unit touches a predetermined substance existing in-vivo. For instance, the medicine information transmitting unit can involve using means including power generating means that starts generating power upon touching the substance existing in-vivo, and means detecting that the unit enters the body when power supply from the power generating means is started.

Furthermore, the second type medicine information transmitting unit can involve using a unit having a module becoming a status of not transmitting the medicine information when short-circuited is covered with a substance disappearing by reacting on a digestive enzyme existing in the predetermined part.

BRIEF DESCRIPTION OF THE DRAWINGS

FIG. 5 is an explanatory diagram of a medicine database held by the ingestion state management device according to the first embodiment;

FIG. 6 is an explanatory diagram of a patient database held by the ingestion state management device according to the first embodiment;

FIG. 7 is a flowchart of an ingestion state examining process executable by the medicine ingestion state management device according to the first embodiment;

FIG. 8 is a flowchart of a process executed with respect to each ingestion medicine information group during the ingestion state examining process;

FIG. 9 is an explanatory diagram of an examination result screen displayed during the ingestion state examining process;

BEST MODE FOR CARRYING OUT THE INVENTION

First Embodiment

A medicine ingestion state management method according to a first embodiment of the invention is a method enabling management of a medicine ingestion state of each individual patient in away that prescribes a medicament having a special composition to each patient.

Therefore, to start with, a composition of a medicine used for the medicine ingestion state management method according to the first embodiment of the invention, will hereinafter be described with reference to the drawings in FIGS. 1 through 3.

Figure 1:
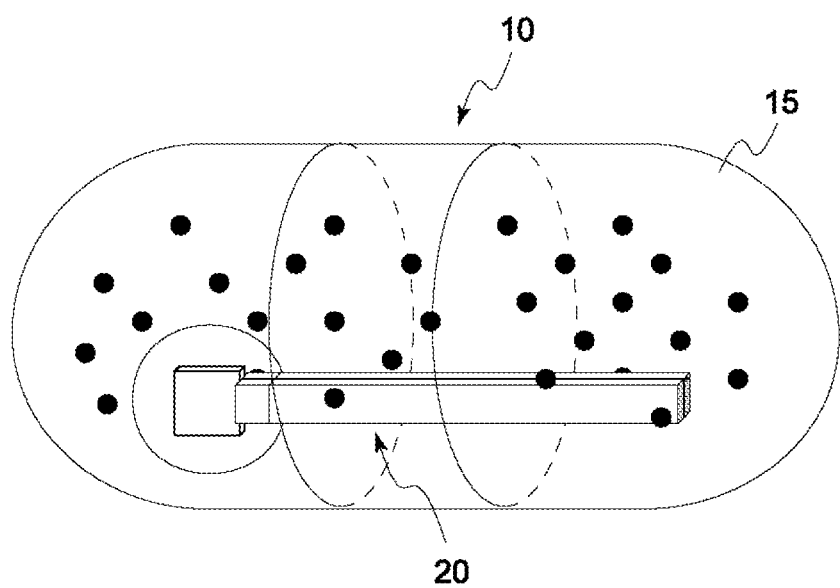
FIG. 1 is an explanatory diagram of a configuration of a medicine used for a medicine ingestion state management method according to a first embodiment of the present invention.

As illustrated in FIG. 1, the medicine 10 employed for the medicine ingestion state management method according to the first embodiment, is a medicine, wherein a powdery or granular medicament (depicted by black solid circles in FIG. 1) and a medicine information transmitting unit 20 are encapsulated by a capsule 15 made from a material dissolvable within the stomach.

Figure 2:
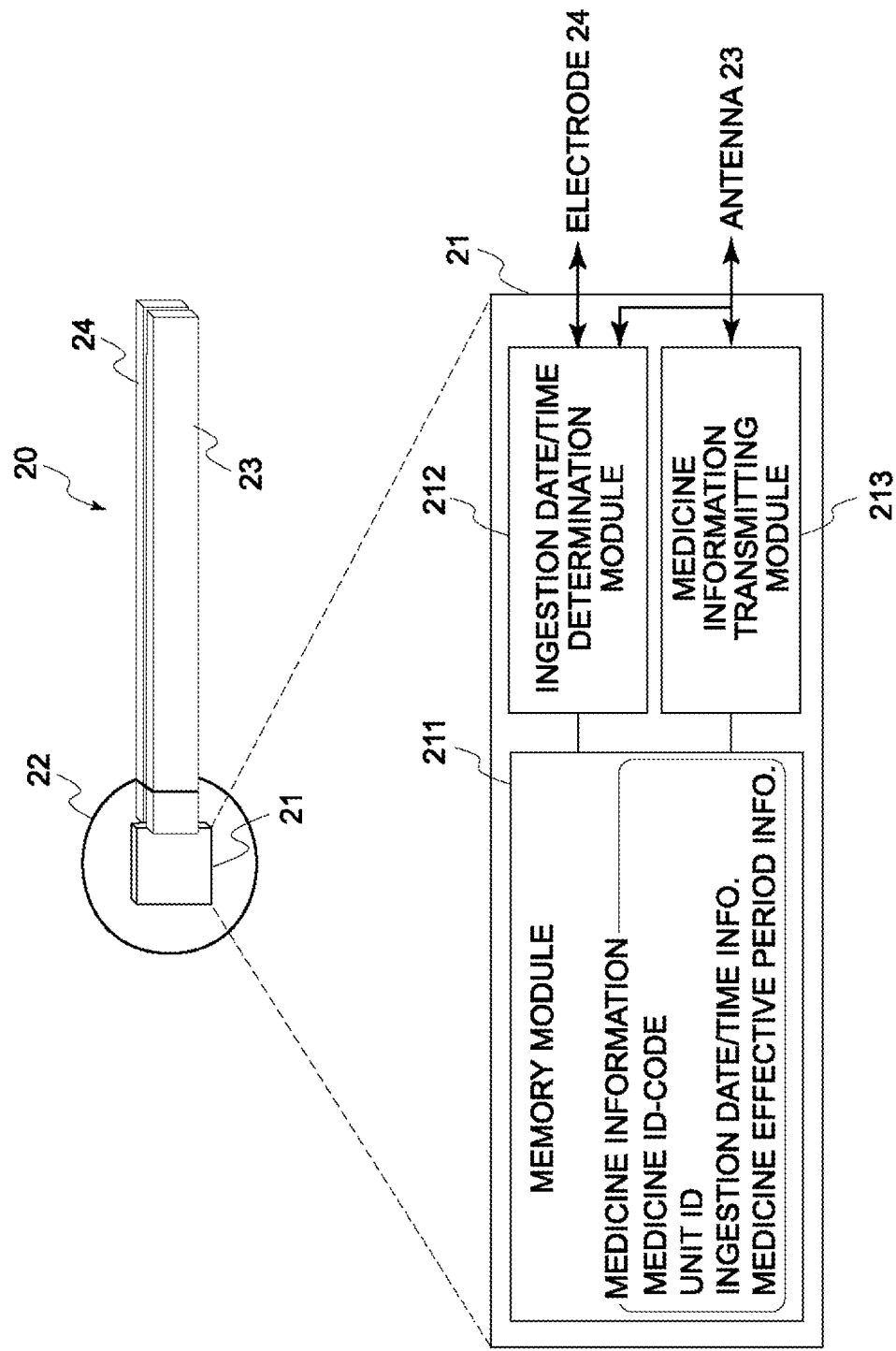
FIG. 2 is an explanatory diagram of a configuration of a medicine information transmitting unit encapsulated in the medicine according to the first embodiment.
Figure 3:
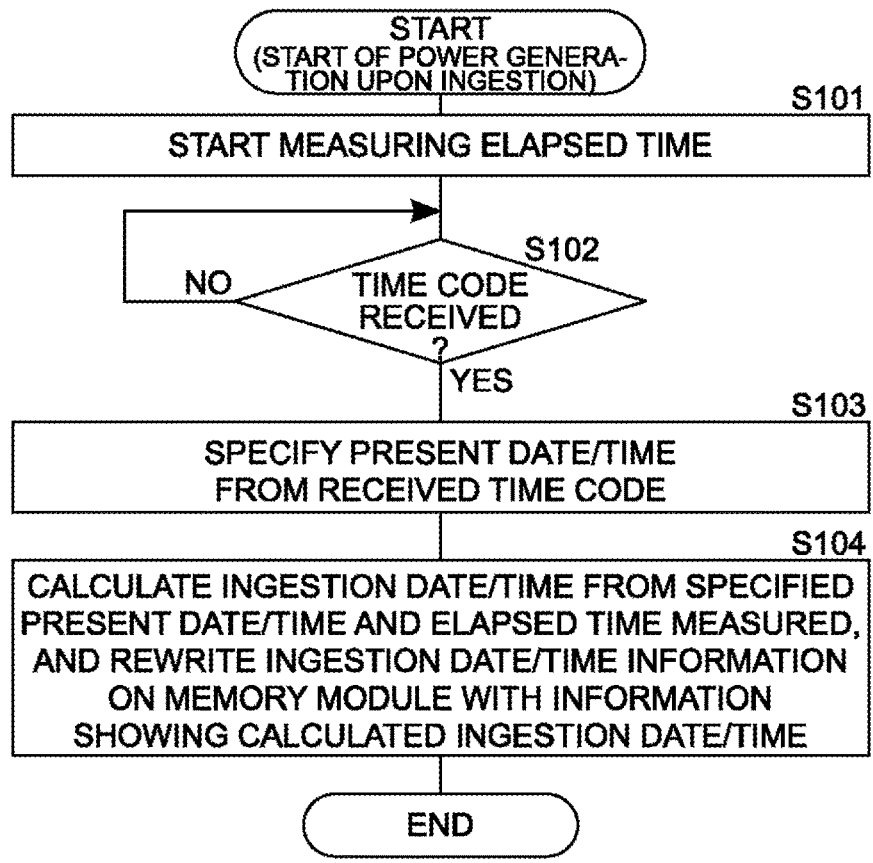
FIG. 3 is a flowchart showing an operation procedure of an ingestion date/time determination module within the medicine information transmitting unit according to the first embodiment.

The medicine information transmitting unit 20 occluded (encapsulated) into the medicine 10 is, as schematically shown in FIG. 2, a unit having an in-vivo undissolvable protection member 22 that covers an IC chip 21 formed with a memory module 211 serving as a storage means, an ingestion date/time determination module 212 serving as a date/time specifying means and a medicine information transmitting module 213 serving as a medicine information transmitting means, the chip 21 being attached with an antenna 23 and an electrode 24 as a detection means and as a power generation means.

It is to be noted that the medicine information transmitting unit 20 according to the first embodiment is a unit, wherein the IC chip 21 is approximately 0.3 mm×0.3 mm in its size, the antenna 23 and the electrode 24 are each approximately 5 mm in their lengths, and the protection member 22 involves using polyester or silicon as a material.

The memory module 211 provided on the IC chip 21 of the medicine information transmitting unit 20 is classified as a rewritable nonvolatile memory (which is an EEPROM (Electrically Erasable Programmable Read Only Memory) in the first embodiment). Further, the medicine information transmitting module 213 is a module supplied via the antenna 23 with electric power from a reader unit 31 (see FIG. 4) that will be explained later on. The medicine information transmitting module 213 is also a module reaching a process-enabled status of executing, when supplied with the power from the reader unit 31, a process of transmitting the medicine information consisting of a medicine identifying code, a unit ID, ingestion date/time information and medicine effective period information that are stored on the memory module 211, and an information write process of rewriting the medicine information stored on the memory module 211 into information designated from by the reader unit 31. Further, the medicine information transmitting module 213 is a multi-accessible module.

Then, the medicine 10 according to the first embodiment is delivered in a state, wherein the memory module 211 of the medicine information transmitting unit 20 encapsulated therein is stored with the medicine information code defined as information for specifying contents (a type and a quantity) of the medicament occluded into the medicine 10, the unit ID uniquely specifying the medicine 10 (in the first embodiment, one medicine 10 contains the single medicine information transmitting unit 20, and therefore it follows that the unit ID uniquely specifies the individual medicine information transmitting unit 20 among a multiplicity of medicine information transmitting units 20 having the same medicine identification code), the ingestion date/time information showing a date and time when the medicine 10 was ingested ("null" is, however, entered in this information field be fore the ingestion), and the medicine effective period information defined as information showing a medicine effective period (usage period) of the medicine.

More specifically, the medicine 10 is manufactured in such a way that after manufacturing the medicament having the composition illustrated in FIG. 1, the medicine information transmitting unit 20, of which the memory module 211 gets stored with those items of medicine information through the execution of the information rewrite process by the medicine information transmitting module 213 of the medicine information transmitting unit 20, is encapsulated together with the medicament into the capsule 15.

As obvious from the description made so far, the memory module 211, the medicine information transmitting module 213 and the antenna 23 of the medicine information transmitting unit 20 are respectively components employed also in a transponder (a passive type of device (an IC tag) which is information-writable and multi-accessible) of an existing RFID (Radio Frequency Identification) system.

By contrast, neither the ingestion date/time determination module 212 nor the electrode 24 of the medicine information transmitting unit 20 is a component used in the transponder of the existing RFID system.

To be specific, the electrode 24 is the in-vivo (in gastric juice) component for building up a battery of which an anode is the antenna 23 and of which a cathode is the electrode 24. Then, the ingestion date/time determination module 212 is a module that starts, when the electrode 24 and the antenna 23 start functioning as the battery (when supplied with the power as a result of the ingestion of the medicine 10 and as a result of the dissolution of the capsule 15), the processes in a procedure shown in FIG. 3.

Namely, the ingestion date/time determination module 212, which starts being supplied with the power, after a start of counting elapse time (step S101), reaches a status of monitoring that a time code is received (step S102). Note that the time code connotes information, representing the present time by an electromagnetic radiation means, such as information (representing the time displayed momentarily at an interval of 60 sec) representing the present time, which is carried on the standard-frequency-and-time-signal-waves transmitted by the standard-frequency-and-time-signal-wave transmission station of the Communications Research Laboratory.

When receiving the time code (step S102; YES), the ingestion date/time determination module 212 decodes the received time code and specifies the present date/time (step S103). Subsequently, the ingestion date/time determination module 212 computes injection date/time when starting counting the elapse time from the specified present date/time and from a now-counting elapse time, and updates the injection date/time information on the memory module 211 with the information representing this ingestion date/time (step S104). Then, the ingestion date/time determination module 212 finishes the operation (comes to a status of executing nothing particular).

In short, the ingestion date/time determination module 212 and the electrode 24 are the components mounted on the medicine information transmitting unit 20 in order to provide the function of updating (rewriting) the ingestion date/time information (the information to be transmitted as an element of the medicine information) on the memory module 211 into the information showing the date/time when the patient actually ingested the medicine 10.

Figure 4:
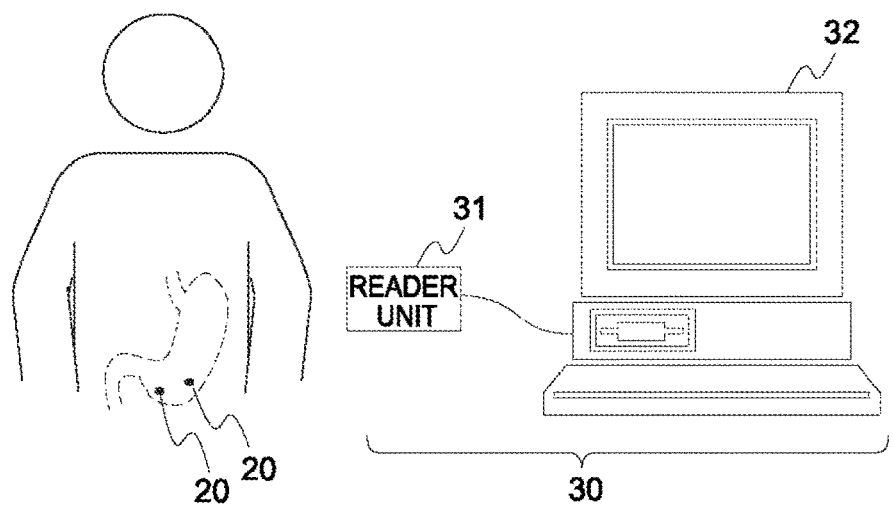
FIG. 4 is an explanatory view of a medicine ingestion state management device employed for the medicine ingestion state management method according to the first embodiment.

Then, the medicine ingestion state management method according to the first embodiment of the invention involves an operation of prescribing the medicine 10 having the composition described above to each individual patient and an operation of grasping the medicine ingestion state of each individual patient, wherein these operations are conducted by utilizing a medicine ingestion state management device 30 installed in each place (which is normally an interior of a hospital) and configured as shown in FIG. 4.

The reader unit 31 serving as a wireless communication device configuring this medicine ingestion state management device 30 is a unit having the same function as the reader (for the passive type multi-accessible transponder) of the existing RFID system has. A computer 32 is a computer of which a HDD is stored with a medicine ingestion state management program, a medicine management database and a patient database, or is a computer so configured as to get accessible to the medicine management database and the patient database via a network by executing the medicine ingestion state management program.

Further, the medicine management database stored within the computer 32 is a database stored, as schematically shown in FIG. 5, with a product name, ingredients/potencies (a type and a quantity) and an in-vivo effective period (a duration of the medicine effect after the in-vivo ingestion) of a certain medicine, a medicine identification code and ingredients of a should-not-be-employed medicine in combination with the former medicine in away that associates these items with the medicine identification code. Namely, from on this medicine management database, the product name and the ingredients/potencies of the now-occluded/used-to-be occluded medicament within the medicine 10 together with the medicine information transmitting unit 20 can be specified from the medicine identification code contained in the medicine information transmitted by a certain medicine information transmitting unit 20, and the medicine identification code, the ingredients, etc of the should-not-be-employed medicine in combination with the above medicine can be also specified.

The patient database is a database stored with, as schematically illustrated in FIG. 6, basic information (consisting of a name, a distinction of sex, a date of birth, an address, etc) about each individual patient, information on a medical history, information on whether the patient is allergic or not, information on whether the patient is pregnant or not, prescription record information consisting of some items of prescription information, ingestion state examination record information consisting of some items of examination result information (of which details will be explained later on), etc in a format enabling these items of information to be retrieved based on the patient ID etc assigned to the patient. Note that the prescription information connotes information inputted by an operator (who is normally a physician) of the medicine ingestion state management device 30 and representing a content of an instruction given to the patient by the operator.

Then, the medicine ingestion state management program is a program enabling the computer 32 (the medicine ingestion state management device 30) to execute an ingestion state examining process in a procedure shown in FIG. 7. It should be noted that the medicine ingestion state management program is a program enabling the computer 32 to execute, other than this ingestion state examining process, a process of adding the prescription information inputted by the operator to the patient database, and a process of searching the medicine management database and the patient database for a category of information instructed by the operator and displaying the retrieved information. The ingestion state examining process, of which the procedure is shown in FIG. 7, is started when starting the examination of the medicine ingestion state (when performing a predetermined operation) after the operator has effected an operation (such as inputting the patient ID associated with the examination subject patient) for designating the examination subject patient upon the computer 32 kept in a status where the medicine ingestion state management program is executed.

To be specific, the computer 32 staring the ingestion state examining process as a result of being given the instruction that the medicine ingestion state should be examined, at first, executes a process of collecting pieces of medicine information from all the medicine information transmitting units 20 existing within a communicable range of the reader unit 31 by use of the reader unit 31 (step S201). Note that the process in step S201 is executed in a state where the reader unit 31 is directed to the examination subject patient (the examination subject patient exists within the communicable range of the reader unit 31). Accordingly, in step S201, the medicine information is collected from all the medicine information transmitting units 20 (the medicine information transmitting unit 20 provided within the medicine 10 with the capsule 15 dissolved, and the medicine information transmitting unit 20 with the medicine encapsulated into the same capsule 15 and then kept in a standby status for being discharged outside the body after a termination of the in-vivo effective period) existing in the in-vivo parts of the examination subject patients, and from the medicine information transmitting units 20 existing in all the not-yet-ingested medicines 10 held by the examination subject patients, respectively (which corresponds to a medicine information collecting step and medicine information receiving means).

The computer 32 finishing the process in step S201 executes, based on the collected medicine information, a process of judging whether or not the medicine that should not be used (ingested) at the same point of time is included in a combination of medicines to be ingested and held by the examination subject patient and whether or not the examination subject patient ingests the medicine as prescribed in a way that refers to the medicine database and the patient database (step S202) (corresponding to a grasping step and search means).

Specifically, in step S202, the computer 32 functions as follows.

To begin with, the computer 32 judges whether or not "null" is entered in the ingestion data/time information (field) in each record of the collected medicine information. Then, the computer 32 stores each record of the medicine information with "null" entered in the ingestion data/time information field as the medicine information (which will hereinafter be referred to as the on-hold medicine information) about the on-hold medicine (which is the medicine 10 held by the examination subject patient), and also stores each record of the medicine information with "null" not entered in the ingestion data/time information field as the medicine information (which will hereinafter be referred to as the in-vivo medicine information) about the in-vivo medicine (which is the medicine 10 ingested by the examination subject patient).

Subsequently, the computer 32 categorizes the thus-stored ingestion medicine information into some groups each consisting of one or more records of ingestion medicine information each having the same medicine identification code, and also categorizes the thus-stored on-hold medicine information into some groups each consisting of one or more records of on-hold medicine information each having the same medicine identification code.

Thereafter, the computer 32 executes processes in a procedure shown in FIG. 8 with respect to each group concerning the ingestion medicine information.

To start with, the computer 32 reads, from the medicine database (see FIG. 5), various items of information (such as the name of the product, the in-vivo effective period and the uncombinable medicine/ingredient) associated with the medicine identification code (which will hereinafter be termed a target medicine identification code) contained in common in each record of the ingestion medicine information belonging to a processing target group (which will hereinafter be referred to as a target ingestion medicine information group) (step S301). Subsequently, the computer 32 judges, based on the grasped in-vivo effective period, the present date/time and the ingestion date/time information contained in each record of the ingestion medicine information, whether or not the medicine associated with each record of the ingestion medicine information belonging to the target ingestion medicine information group exists in an in-vivo effective state, and stores a judgment result (step S302).

Moreover, the computer 32 executes a process of judging, based on the target medicine identification code, the ingestion date/time information contained in each record of the ingestion medicine information belonging to the target ingestion medicine information group and the prescription record information on the examination subject patient within the patient database, whether or not the associated medicine is prescribed to the examination subject patient or is ingested as prescribed, and storing a judgment result (step S303). The computer 32 also executes a process of judging whether or not the information on the uncombinable medicine/ingredient read from the medicine database contains the information matching with the medicine identification code contained in each record of the ingestion medicine information/on-hold medicine information belonging to other groups, and stores a judgment result (step S303). It should be noted that the computer 32 executes also, though not shown, a process of judging whether or not there expires the medicine effective period specified by the medicine effective period information contained in each record of the ingestion medicine information belonging to the target ingestion medicine information group, and storing a judgment result.

After executing these processes with respect to each target ingestion medicine information group, the computer 32 executes a process of reading, from the medicine database, with respect to each group about the on-hold medicine information, the various items of information associated with the medicine identification code contained in common in each record of the ingestion medicine information belonging to this group, a process of judging whether or not the information on the uncombinable medicine/ingredient read from the medicine database contains the information matching with the medicine identification code contained in each record of the ingestion medicine information/on-hold medicine information belonging to other groups or information matching with a medicine identification code of a certain medicine having a possibility of being prescribed hereafter and storing a judgment result, and a process of judging whether or not there expires the medicine effective period specified by the medicine effective period information contained in each record of the ingestion medicine information belonging to the group, and storing a judgment result.

Then, the computer 32, which has executed the processes of those contents in step S202 (FIG. 7), executes, in subsequent step S203, an examination result screen display process defined as a process for displaying to the operator the examination/judgment results given by the processes in step S202 (which corresponds to information output means).

To be specific, when performing this examination result screen display process, the computer 32 at first displays the examination result screen of the contents as shown in FIG. 9 on the display. Namely, the computer 32 displays the examination result screen showing whether or not the medicine that should not be used (ingested) at the same point of time is included in the combination of medicines to be ingested and held by the examination subject patient and whether or not the examination subject patient ingests the medicine as prescribed.

Thereafter, the computer 32 comes to a standby status for waiting for a "reexamination" button and a "prescription input screen" button to be pressed on this examination result screen. Then, the computer 32, when the "prescription input screen" button is pressed, finishes the examination result screen display process, and, after adding to the patient database the examination result information consisting of the information representing the examination/judgment results and the information representing the date/time of the scheduled day as the information about the examination subject patient (step S204), finishes the processes in FIG. 7 (i.e., a process for accepting an input of the information about the prescription is started).

Note that the "reexamination" button is a button that should be pressed by the operator if the examination gets into a failure due to some cause. When this "reexamination" button is pressed, though a description in the flowchart is omitted, the computer 32, after clearing the examination result (the information obtained by the process in step S202), terminates the examination result screen display process, and resumes the processes from step S201.

As explained above, in the medicine ingestion state management method according to the first embodiment, the medicine 10 is prescribed for each individual patient, wherein the medicine 10 contains the medicament and the encapsulated medicine information transmitting unit 20 for transmitting the medicine information enabling the type and the quantity of the medicament to be specified. Hence, according to the medicine ingestion state management method, it is possible to grasp which medicine is actually ingested by the patient without hearing the information on the ingestion medicine from the patient, and therefore it follows that the proper prescription is always made.

Moreover, the medicine information transmitted by the medicine information transmitting unit 20 includes the ingestion date/time information showing the date and time when the medicine was ingested. Therefore, according to the medicine ingestion state management method, it follows that it is feasible to make the more proper prescription (based on the greater items of information) than in the case of recognizing only which medicine is ingested by each individual patient. Furthermore, it is also possible to grasp whether or not the each medicine is ingested as prescribed.

Further, the medicine information transmitted by the medicine information transmitting unit 20 is the information taking a value different after and before the ingestion of the medicine, and hence, according to the medicine ingestion state management method in the first embodiment, it can be examined at one time which medicament (the medicine 10) is ingested or held. Moreover, the medicine information transmitted by the medicine information transmitting unit 20 contains the medicine effective period, whereby the medicament (the medicine 10) of which the medicine effective period expires can be easily identified.

Second Embodiment

The medicine ingestion state management method according to a second embodiment of the present invention is similar to the medicine ingestion state management method according to the first embodiment. Therefore, in the following discussion, a content of the medicine ingestion state management method according to the second embodiment will be described in away that puts a focus on a difference from the medicine ingestion state management method according to the first embodiment.

Figure 10:
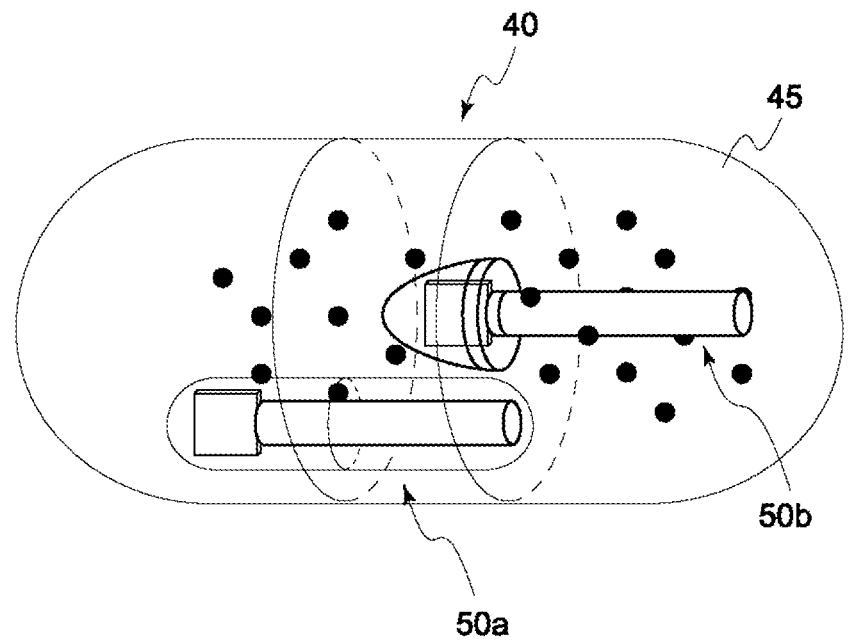
FIG. 10 is an explanatory diagram of a configuration of the medicine used in a medicine ingestion state management method according to a second embodiment of the present invention.

The medicine ingestion state management method according to the second embodiment is a method conducted by use of a medicine 40 having a composition illustrated in FIG. 10.

Namely, the medicine 40 is a medicine, wherein a medicament exhibiting it a medicament effect by absorption in the intestine (depicted by black solid circles in FIG. 10), a first type medicine information transmitting unit 50a and a second type medicine information transmitting unit 50b are encapsulated by a capsule 45 made from a material dissolvable within the stomach.

Figure 11:
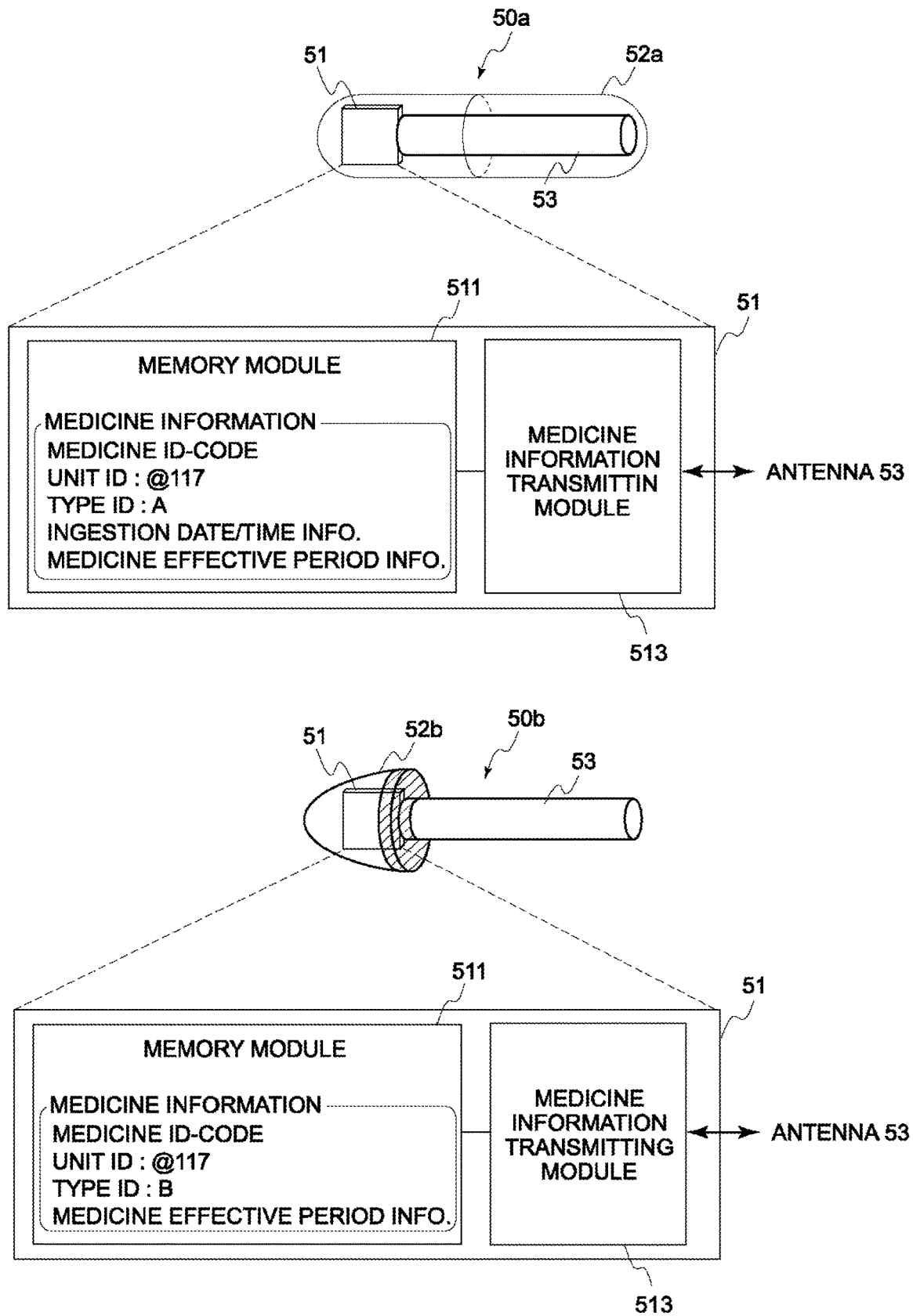
FIG. 11 is an explanatory diagram of configurations of a first type medicine information transmitting unit and of a second type medicine information transmitting unit according to the second embodiment.

The first type medicine information transmitting unit 50a occluded (encapsulated) into the medicine 40 is, as schematically shown in FIG. 11, a unit having an in-vivo undissolvable protection member 52a that covers an IC chip 51 formed with a memory module 511 and a medicine information transmitting module 513, the chip 21 being attached with an antenna 53.

The IC chip 51 used for the first type medicine information transmitting unit 50a is a chip substantially corresponding to the IC chip 21 (see FIG. 2). Namely, the memory module 511 and the medicine information transmitting module 513 formed on the IC chip 51 are the same as the memory module 211 and the medicine information transmitting module 212 formed on the IC chip 21 except such a point that the medicine information to be stored and transmitted contains a type ID. Note that the type ID is information specifying which unit, the first type medicine information transmitting unit 50a (the type ID="A") or the second type medicine information transmitting unit 50b (the type ID="B"), the self-unit corresponds to. A combination of the type ID="A" and a unit ID=@117, corresponds to first identifying information.

On the other hand, the second type medicine information transmitting unit 50b is a unit having basically the same configuration as the first type medicine information transmitting unit 50a has, however, part (depicted by hatching in FIG. 11) of the protection member 52b covering the IC chip 51 involves using a substance reacting on a digestive enzyme existing in only an alimentary canal where the medicament is absorbed. In short, the second type medicine information transmitting unit 50b is constructed such that shortly after entering the body, part of the IC chip 51 is brought into contact with an in-vivo water content, and, as a result of this, a circuit is short-circuited (so as not to transmit the medicine information). Accordingly, when one medicine 40 is ingested, the medicament reaches a specified in-vivo part together with the second type medicine information transmitting unit 50b and exhibits the medicament effect. Then, part of the protection member 52b of the second type medicine information transmitting unit 50b is dissolved, with the result that the IC chip 51 of the second type medicine information transmitting unit 50b is short-circuited. Thereafter, the medicament effect of this medicament expires after en elapse of in-vivo effective period. Namely, the actual medicament effective period of the medicament in the medicine 40 is a length from a point of time when the IC chip 51 of the second type medicine information transmitting unit 50b is short-circuited up to a point of time after the in-vivo effective period.

The first type medicine information transmitting unit 50a and the second type medicine information transmitting unit 50b, which are encapsulated in the same medicine 40, are coincident with each other in terms of their medicine identification code and the unit ID stored as the medicine information on the memory module 511 but are, as described above, different in their type IDs from each other. A combination of the type ID="B" and the unit ID=@117 corresponds to second identifying information.

Figure 12:
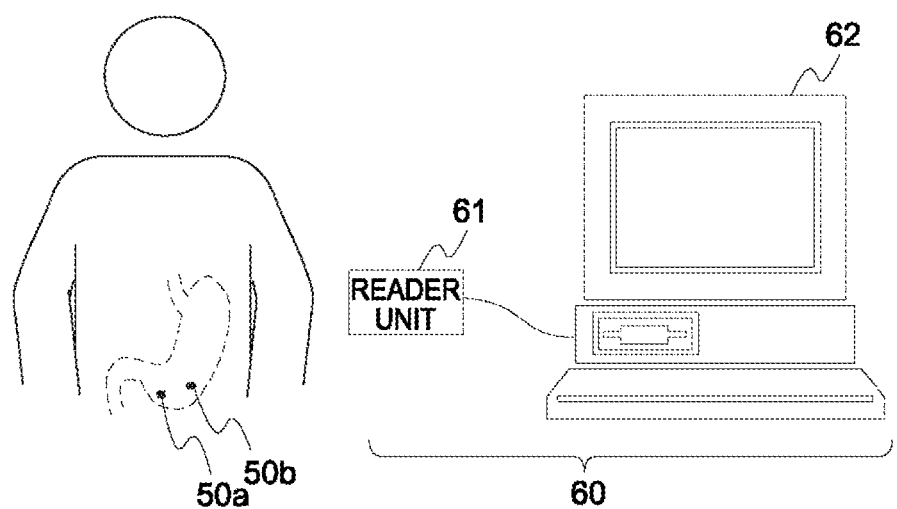
FIG. 12 is an explanatory diagram of a medicine ingestion state management device employed in the medicine ingestion state management method according to the second embodiment.

Then, the medicine ingestion state management method according to the second embodiment of the present invention involves an operation of prescribing the medicine 40 having the composition described above to each individual patient and an operation of grasping the medicine ingestion state of each individual patient, wherein these operations are conducted by utilizing a medicine ingestion state management device 60 installed in each place (which is normally an interior of the hospital) and configured as shown in FIG. 12.

Figure 13:
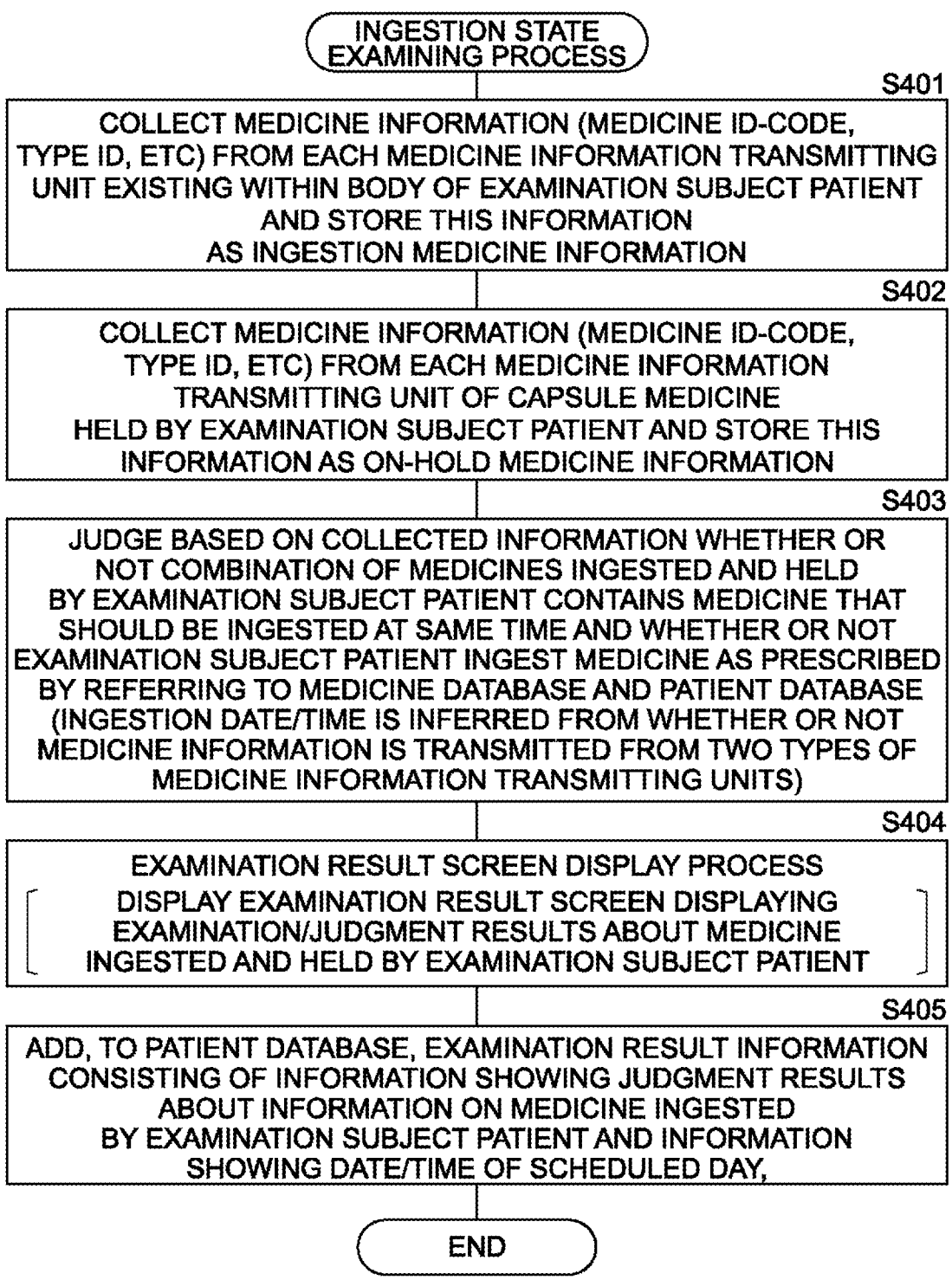
FIG. 13 is a flowchart of the ingestion state examining process executable by the medicine ingestion state management device according to the second embodiment.

This medicine ingestion state management device 60 is a modified version of the medicine ingestion state management device 30 so as to execute an ingestion state examining process in a procedure shown in FIG. 13 when given an instruction that the medicine ingestion state should be examined.

To be specific, a computer 62 (the medicine ingestion state management device 60) given the instruction that the medicine ingestion state should be examined, at first executes a process of collecting the medicine information from all of medicine information transmitting units 50 (first type medicine information transmitting units 50a or second type medicine information transmitting units 50b) existing the in-vivo part of the examination subject patient by use of a reader unit 61, and storing the collected information as ingestion medicine information (step S401) (which corresponds to a medicine information collecting step and medicine information receiving means). Subsequently, the computer 62 executes a process of collecting the medicine information from all the medicine information transmitting units 50 held by the examination subject patient by use of the reader unit 61 and storing the collected information as the on-hold medicine information (step S402) (which corresponds to on-hole medicine information receiving means).

It should be noted that the process in step S401 is a process executed after making the examination subject patient present all the on-hold medicines 40 and placing these medicines 40 in a position that is away from the examination subject patient (beyond a communicable range of the reader unit 61 directed to the examination subject patient). Further, a process in step S402 is a process executed after directing the reader unit 61 to the medicines 40 placed in the position that is away from the examination subject patient.

Then, the computer 62 finishing the processes in steps S401 and S402 executes, based on the collected ingestion medicine information/on-hold medicine information, a process of judging whether or not the medicine that should not be used (ingested) at the same point of time is included in a combination of medicines to be ingested and held by the examination subject patient and whether or not the examination subject patient ingests the medicine as prescribed in away that refers to the medicine database and the patient database (step S403) (which corresponds to a grasping step and search means).

Specifically, in step S403, the computer 62 categorizes the ingestion medicine information into some groups each consisting of one or more records of ingestion medicine information each having the same medicine identification code, and also categorizes the on-hold medicine information into some groups each consisting of one or more records of on-hold medicine information each having the same medicine identification code. Thereafter, the computer 62 executes the following processes with respect to each of the groups about the ingestion medicine information.

To begin with, the computer 62 searches through the medicine database by employing, as a search key, the medicine identification code (which will hereinafter be referred to as a target medicine identification code) contained in common in each record of the ingestion medicine information belonging to a processing target group (which will hereinafter be referred to as a target ingestion medicine information group), thereby grasping a product name, an in-vivo effective period, etc that are associated with each record of the ingestion medicine information.

Further, the computer 62 specifies, within the target ingestion medicine information group, an in-vivo medicine count N1 in the ingestion medicine information (containing a first type ID="A") transmitted by the first type medicine information transmitting unit 50a, and specifies a medicine count N2 in the ingestion medicine information (containing a second type ID="B") transmitted by the second type medicine information transmitting unit 50b. As a result, the computer reckons the in-vivo medicines 40 existing in the examination subject patient to be N1 and reckons the now-effect-keeping medicines 40 in the in-vivo medicines 40 to be (N1-N2). Then, the computer 62 specifies the product name, the ingredients, the potencies (the type and the quantity) that are associated with the medicine identification code in common in each record of the ingestion medicine information by referring to the medicine database.

Moreover, the computer 62, in away that uses, as a search key, the target ingestion medicine identification code of the medicine 40 of which one or more medicaments are judged to be now keeping the medicine effect, executes a process of judging whether or not the information on the uncombinable medicine/ingredient that is read from the medicine database contains the information associated with the medicine identification code contained in each record of the ingestion medicine information/on-hold medicine information belonging to some other group or associated with the medicine identification code on the medicine having a possibility of being prescribed hereafter and storing a result of the judgment, and a process of judging whether the period specified by the medicine effective period information contained in each record of the ingestion medicine information expires or not and storing a result of the judgment.

Further, the computer 62 executes, with respect to each group about the on-hold medicine information, a process of reading from the medicine database the various items of information associated with the medicine identification code contained in common in each record of the ingestion medicine information belonging to this group, a process of judging whether or not the information on the uncombinable medicine/ingredient that is read from the medicine database contains the information associated with the medicine identification code contained in each record of the ingestion medicine information/on-hold medicine information belonging to some other group and storing a result of the judgment, and a process of judging whether the period specified by the medicine effective period information contained in each record of the ingestion medicine information belonging to this group expires or not and storing a result of the judgment.

The computer 62 executing the processes having these contents in step S403 executes, in subsequent step S404, an examination result screen display process of displaying, though similar to the examination result screen, an examination result screen displaying "N1" and "N1-N2" as pieces of information corresponding to the quantity of the in-vivo effective medicine and the ingestion state (corresponding to an information output means). Then, the computer 62, when the "prescription input screen" button on the examination result screen is pressed, finishes the examination result screen display process. Then, the computer 62 adds the examination result information consisting of the information representing the examination/judgment result and the date/time of the scheduled day as the information about the examination subject patient to the patient database (step S405), and thereafter terminates the processes in FIG. 13 (which means a start of the process of accepting the input of the information on the prescription).

As obvious from the discussion given above, according to the medicine ingestion state management method according to the second embodiment, also in the case of the medicine 40 occluding the medicaments absorbed in the intestine, it is also specify the type and the quantity of the medicament that now exhibits the medicine effect in the intestine. Hence, when such a medicament is ingested, it is feasible to specify the medicament that must not be simultaneously ingested in terms of compatibility.

Modified Example

The medicine ingestion state management methods according to the first embodiment and the second embodiment can be modified in a variety of forms. For example, the medicine information transmitting unit 20 encapsulated into the medicine 10 may be configured by mounting a battery in the IC chip 21 instead of providing the electrode 24. Further, in the second embodiment, as a substitute for the first type medicine information transmitting unit 50a, there may be employed a unit corresponding to the medicine information transmitting unit 20 including the electrode 24 and the ingestion date/time determination module 212.

Moreover, the medicine 40 may be modified into a medicine encapsulating one single unit having the function as the first type medicine information transmitting unit 50a and the function as the second type medicine information transmitting unit 50b. Note that such a unit can be manufactured simply by, for example, connecting two pieces of chips 51 to one antenna 53, and covering one chip 51 with the protection member 52a and the other chip 51 with the protection member 52b. Further, such a unit can be manufactured also by setting the chip 51 in such a status as to output a different category of medicine information when a certain part is short-circuited.

Furthermore, as a matter of course, the medicine information transmitting units 20 and 50 may be configured to transmit the medicine information showing more detailed contents, and the medicine ingestion state management devices 30 and 60 may be constructed to display the examination result screen displaying contents different from those described above.

Still further, respectively in the first and second embodiments, the capsule medicines configured by encapsulating the medicine information transmitting units 20 and 50 have been exemplified by way of the specific examples of the medicines 10 and 40, however, for instance, even medicines configured by incorporating the medicine information transmitting units 20 and 50 together with tablets or granular medicaments into divided pieces of wrap, become objects of the present invention.

What is claimed is:

1. A capsule comprising;
   a medicament; and
   an IC chip which transmits information to outside of a body of a patient who ingests the medicament, the IC chip being covered with a first material which is not dissolved within the patient's body, and
   wherein the IC chip and the medicament are combined with a second material dissolvable within the patient's stomach,
   wherein the IC chip is connected to an electrode in the capsule and starts a given operation using power generated by exposure of the electrode to gastric juice, and
   wherein the exposure of the electrode to the gastric juice is caused by dissolution of the second material by the gastric juice.

2. The capsule according to claim 1, wherein the IC chip transmits information indicating a type of the medicament.

3. The capsule according to claim 1, wherein the IC chip includes a first module that counts a length of time elapsed from when the capsule dissolved within the patient's body, and a second module that transmits information calculated from the length of time which is counted by the first module.

4. The capsule according to claim 3, wherein the first module starts counting the length of time elapsed when power is supplied to the IC chip as a result of dissolution of the capsule within the patient's stomach.

5. The capsule according to claim 3, further comprising an electrode connected to the IC chip, wherein the electrode functions as a battery by immersion into body fluid.

6. The capsule according to claim 3, wherein the second module transmits medicine information containing information representing a medicine effective period of the medicament.

7. The capsule according to claim 1, wherein the IC chip includes:
   a first IC chip; and
   a second IC chip,
   wherein the first IC chip is covered with the first material, and the second IC chip is partly covered with a second material which responds to body fluid within the patient's body.

8. The capsule according to claim 7, wherein the first IC chip transmits first identifying information, the second IC chip transmits second identifying information, and the first identifying information and second identifying information include the same information about the medicament.

9. A capsule which can be swallowed and encapsulates a medicament, the capsule being made from a first material dissolvable within a stomach, the capsule comprising:
   an IC chip covered with a second material which does not dissolve in a human body and encapsulated with the medicament in the capsule,
   wherein the IC chip is connected to an electrode in the capsule and includes
   a memory;
   a module that writes information into the memory, wherein the module starting writing after power is supplied from the electrode to the IC chip as a result of dissolution of the capsule in the stomach; and a transmitting module that transmits information stored in the memory, using the power, wherein the power is generated by exposure of the electrode to gastric juice, and wherein the exposure of the electrode to the gastric juice is caused by dissolution of the first material by the gastric juice.

10. The capsule according to claim 9, wherein the information includes an identifier of a unit on which the IC chip is equipped.

11. The capsule according to claim 9, wherein the memory stores information which changes from before swallowed to after swallowed.

12. A medicine ingestion state management system, comprising:

a database storing prescription information;

a combination of a medicament and an IC chip, the combination being made using a material that is soluble by gastric juice, the IC chip is connected to an electrode, and receives power generated by exposure of the electrode to the gastric juice, and the IC chip transmits medicine information using the power;

a wireless communication device configured to receive the medicine information transmitted from the IC chip;

a computer configured to determine whether or not the patient ingests the medicament as prescribed by referring to the prescription information stored in the database, based on the medicine information received from the IC chip; and a display configured to display a result information indicating whether or not the patient ingests the medicament as prescribed, wherein the exposure of the electrode to the gastric juice is caused by dissolution of the material by the gastric juice.

* * * * *